(12) United States Patent
Dace

(10) Patent No.: US 8,562,650 B2
(45) Date of Patent: Oct. 22, 2013

(54) PERCUTANEOUS SPINOUS PROCESS FUSION PLATE ASSEMBLY AND METHOD

(75) Inventor: Mark C. Dace, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 329 days.

(21) Appl. No.: 13/037,729

(22) Filed: Mar. 1, 2011

(65) Prior Publication Data
US 2012/0226313 A1 Sep. 6, 2012

(51) Int. Cl.
*A61B 17/70* (2006.01)

(52) U.S. Cl.
USPC ........................................................ 606/248

(58) Field of Classification Search
USPC ......... 606/246, 248, 249, 250, 251, 252, 253, 606/259, 261, 280, 70, 71, 282, 286, 297, 606/74, 324, 328; 403/362; 411/393
See application file for complete search history.

(56) References Cited

U.S. PATENT DOCUMENTS

| | | |
|---|---|---|
| 2,677,369 A | 5/1954 | Knowles |
| 3,648,691 A | 3/1972 | Lumb et al. |
| 4,011,602 A | 3/1977 | Rybicki et al. |
| 4,257,409 A | 3/1981 | Bacal et al. |
| 4,554,914 A | 11/1985 | Kapp et al. |
| 4,573,454 A | 3/1986 | Hoffman |
| 4,604,995 A | 8/1986 | Stephens et al. |
| 4,686,970 A | 8/1987 | Dove et al. |
| 4,827,918 A | 5/1989 | Olerud |
| 5,011,484 A | 4/1991 | Breard |
| 5,047,055 A | 9/1991 | Bao et al. |
| 5,092,866 A | 3/1992 | Breard et al. |
| 5,201,734 A | 4/1993 | Cozad et al. |
| 5,306,275 A | 4/1994 | Bryan |
| 5,360,430 A | 11/1994 | Lin |
| 5,366,455 A | 11/1994 | Dove |
| 5,415,661 A | 5/1995 | Holmes |
| 5,437,672 A | 8/1995 | Alleyne |
| 5,454,812 A | 10/1995 | Lin |
| 5,496,318 A | 3/1996 | Howland et al. |

(Continued)

FOREIGN PATENT DOCUMENTS

| | | |
|---|---|---|
| DE | 2821678 A1 | 11/1979 |
| EP | 0322334 B1 | 2/1992 |

(Continued)

OTHER PUBLICATIONS

"Dispositivo Intervertebrale Ammortizzante DIAM," date unknown, p. 1.

(Continued)

*Primary Examiner* — Eduardo C Robert
*Assistant Examiner* — David Comstock

(57) ABSTRACT

A spinal implant helps stabilize vertebrae for fusion. The implant is particularly adapted for percutaneous implantation, but may also be used with other access techniques. The implant includes first and second plates that extend through a slot in a frame. When installed, the frame extends laterally through the interspinous space, and the plates extend superiorly-inferiorly along respective lateral sides of the spinous processes. The plates are moved toward one another and relative to the slot to clamp the implant to the spinous processes. The slot may be variably sized along its length, and the plates may move into differently sized portions of the slot during the clamping process.

20 Claims, 13 Drawing Sheets

(56) References Cited

U.S. PATENT DOCUMENTS

| | | |
|---|---|---|
| 5,609,634 A | 3/1997 | Voydeville |
| 5,628,756 A | 5/1997 | Barker, Jr. et al. |
| 5,645,599 A | 7/1997 | Samani |
| 5,674,295 A | 10/1997 | Ray et al. |
| 5,676,702 A | 10/1997 | Ratron |
| 5,690,649 A | 11/1997 | Li |
| 5,702,452 A | 12/1997 | Argenson et al. |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 6,022,376 A | 2/2000 | Assell et al. |
| 6,048,342 A | 4/2000 | Zucherman et al. |
| 6,068,630 A | 5/2000 | Zucherman et al. |
| 6,132,464 A | 10/2000 | Martin |
| 6,293,949 B1 | 9/2001 | Justis et al. |
| 6,352,537 B1 | 3/2002 | Strnad |
| 6,364,883 B1 | 4/2002 | Santilli |
| 6,402,750 B1 | 6/2002 | Atkinson et al. |
| 6,440,169 B1 | 8/2002 | Elberg et al. |
| 6,451,019 B1 | 9/2002 | Zucherman et al. |
| 6,500,178 B2 | 12/2002 | Zucherman et al. |
| 6,514,256 B2 | 2/2003 | Zucherman et al. |
| 6,582,433 B2 | 6/2003 | Yun |
| 6,626,944 B1 | 9/2003 | Taylor |
| 6,645,207 B2 | 11/2003 | Dixon et al. |
| 6,695,842 B2 | 2/2004 | Zucherman et al. |
| 6,709,435 B2 | 3/2004 | Lin |
| 6,723,126 B1 | 4/2004 | Berry |
| 6,733,534 B2 | 5/2004 | Sherman |
| 6,761,720 B1 | 7/2004 | Senegas |
| 6,835,205 B2 | 12/2004 | Atkinson et al. |
| 6,946,000 B2 | 9/2005 | Senegas et al. |
| 7,041,136 B2 | 5/2006 | Goble et al. |
| 7,048,736 B2 | 5/2006 | Robinson et al. |
| 7,087,083 B2 | 8/2006 | Pasquet et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,604,652 B2 | 10/2009 | Arnin et al. |
| 8,157,842 B2 * | 4/2012 | Phan et al. .................. 606/249 |
| 8,287,569 B1 * | 10/2012 | Powell .......................... 606/248 |
| 2001/0016743 A1 | 8/2001 | Zucherman et al. |
| 2002/0143331 A1 | 10/2002 | Zucherman et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0097931 A1 | 5/2004 | Mitchell |
| 2004/0133280 A1 | 7/2004 | Trieu |
| 2004/0199255 A1 | 10/2004 | Mathieu et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0261768 A1 | 11/2005 | Trieu |
| 2005/0288672 A1 | 12/2005 | Ferree |
| 2006/0004447 A1 | 1/2006 | Mastrorio et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1 | 6/2006 | Taylor |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0043362 A1 | 2/2007 | Malandain et al. |
| 2007/0100340 A1 | 5/2007 | Lange et al. |
| 2007/0123861 A1 | 5/2007 | Dewey et al. |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2010/0121379 A1 | 5/2010 | Edmond |
| 2011/0066186 A1 * | 3/2011 | Boyer et al. .................. 606/249 |

FOREIGN PATENT DOCUMENTS

| | | |
|---|---|---|
| EP | 1138268 A1 | 10/2001 |
| EP | 1330987 A1 | 7/2003 |
| EP | 1854433 A1 | 11/2007 |
| FR | 2623085 A1 | 5/1989 |
| FR | 2625097 A1 | 6/1989 |
| FR | 2681525 A1 | 3/1993 |
| FR | 2700941 A1 | 8/1994 |

(56) References Cited

FOREIGN PATENT DOCUMENTS

| | | |
|---|---|---|
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 98/20939 | 5/1998 |
| WO | WO 2004/047691 A1 | 6/2004 |
| WO | WO 2005/009300 A1 | 2/2005 |
| WO | WO 2005/044118 A1 | 5/2005 |
| WO | WO 2005/110258 A1 | 11/2005 |
| WO | WO 2006/064356 A1 | 6/2006 |
| WO | WO 2007/034516 A1 | 3/2007 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine." date unknown, pp. 1-24, Spine Next, an Abbott Laboratories company, Bordeaux, France.

Benzel et al., "Posterior Cervical Interspinous Compression Wiring and Fusion for Mid to Low Cervical Spinal injuries," J. Neurosurg., Jun. 1989, pp. 893-899. vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites." Maîrise orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St, Louis, Missouri, 1970, Tindall et al., eds., 1971, Ch. 6, pp. 86- 105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132. Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabililtés Dégénératives," Acta Othopaedica Belgica, 1991, pp. 221-226, vol. 57, Suppl. I.

(56) References Cited

OTHER PUBLICATIONS

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Mesing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute international Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86. vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery. Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

PERCUTANEOUS SPINOUS PROCESS FUSION PLATE ASSEMBLY AND METHOD

BACKGROUND

The present invention relates generally to spinal stabilization, and more particularly to spinal fusion implants and procedures for implanting the same, particularly percutaneously.

A wide variety of spinal fusion devices are used following partial or total discectomies for stabilization of the spine at that site. Many such devices are secured extradiscally, such as to the pedicles or spinous processes. For example, the SPIRE brand fusion products available from Medtronic, Inc. of Minneapolis, Minn. are typically secured to the spinous processes. See also the devices and methods disclosed in U.S. Pat. Nos. 7,048,736 and 7,727,233. The implantation of such devices may involve significant muscle dissection and associated surgical time, as they are typically ill suited for minimally invasive surgical techniques. As a result, use of these devices may require significant recovery time. Thus, while numerous spinal fusion stabilization devices have been proposed, there remains a need for alternative approaches, particularly those suited for percutaneous implantation.

SUMMARY

The present invention provides a spinal implant that helps stabilize vertebrae for fusion. The implant is particularly adapted for percutaneous implantation, but may also be used with other access techniques. The implant, in one or more embodiments, includes first and second plates that extend through a slot in a frame. When installed, the frame extends laterally through the interspinous space, and the plates extend superiorly-inferiorly along respective lateral sides of the spinous processes. The plates are moved toward one another and relative to the slot to clamp the implant to the spinous processes.

In some embodiments, the present invention provides a spinal implant device comprising a first plate, a second plate, a frame, and a locking element. The first plate curvingly extends along a first curved longitudinal axis and has a first medial face configured to abut adjacent spinous processes with biting projections thereon. The second plate curvingly extends along a second curved longitudinal axis and has a second medial face configured to abut the adjacent spinous processes with biting projections thereon. The frame extends along a third curved longitudinal axis and has a longitudinal slot therethrough. The first and second plates are disposed through the slot such that the first and second axes are transverse to the third axis and the first and second medial faces face toward each other in spaced relation. The locking element engages a proximal end of the frame and is longitudinally moveable relative to the frame such that longitudinal displacement of the locking element toward a distal end of the frame narrows a distance between the first plate and the second plate. In some embodiments, longitudinal displacement of the locking element toward a distal end of the frame causes the first and second plates to enter relatively narrower sections of the slot. The first plate may comprise first and second end sections, with an intermediate portion disposed therebetween, with the intermediate portion having a reduced cross section relative to the first and second end sections, and with the intermediate section disposed in the slot. The first end section of the first plate may advantageously have a tapered tip portion disposed opposite the intermediate section. The tapered tip portion may have the largest cross section of the first plate. The first plate may comprise an elongate base and the associated biting projections; wherein the base has a substantially D-shaped cross-section normal to the first axis, with the medial face being substantially flat. The second plate may be similar to the first plate, with the first and second plates being substantially mirror images of each other in some embodiments. The slot may have a variable height. For example, the slot may comprise two portions of enlarged height, disposed in longitudinally spaced relation.

In other embodiments, the first plate curvingly extends along a first curved longitudinal axis, and the first plate has a first medial face configured to abut adjacent spinous processes with biting projections thereon. The second plate curvingly extends along a second curved longitudinal axis, and the second plate has a second medial face configured to abut the adjacent spinous processes with biting projections thereon. The curvilinear frame extends along a third curved longitudinal axis and having a longitudinal slot therethrough. The first and second plates are disposed through the slot such that the first and second axes are transverse to the third axis and the first and second medial faces face toward each other in spaced relation. The locking element engages a proximal end of the frame and is longitudinally moveable relative to the frame. The implant is changeable from a first configuration to a second configuration. In the first configuration, the first and second plates are disposed a first distance apart. In the second configuration: the first and second plates are disposed a second distance apart, the second distance less than the first distance; the first and second plates are disposed more distally relative to frame than in the first configuration; the locking element is disposed more distally relative to the frame than in the first configuration. The slot may comprise a distal end, with the first plate abutting the distal end of the slot in the second configuration and the locking element abuts the second plate in the second configuration. The first plate may comprise first and second end sections, with an intermediate portion disposed therebetween, with the intermediate portion having a reduced cross section relative to the first and second end sections, and the intermediate section disposed in the slot. The slot may have variable height, with two spaced apart first sections of enlarged height and two spaced apart second sections of reduced height; one of the second sections of reduced height is disposed between the first sections of enlarged height and one of the first sections is disposed between the second sections. The first and second plates may be disposed in the first sections of the slot in the first configuration and disposed in the second sections of the slot in the second configuration.

In various embodiments, the present invention has one or more of the above attributes, alone or in any combination.

DETAILED DESCRIPTION

Figure 1:
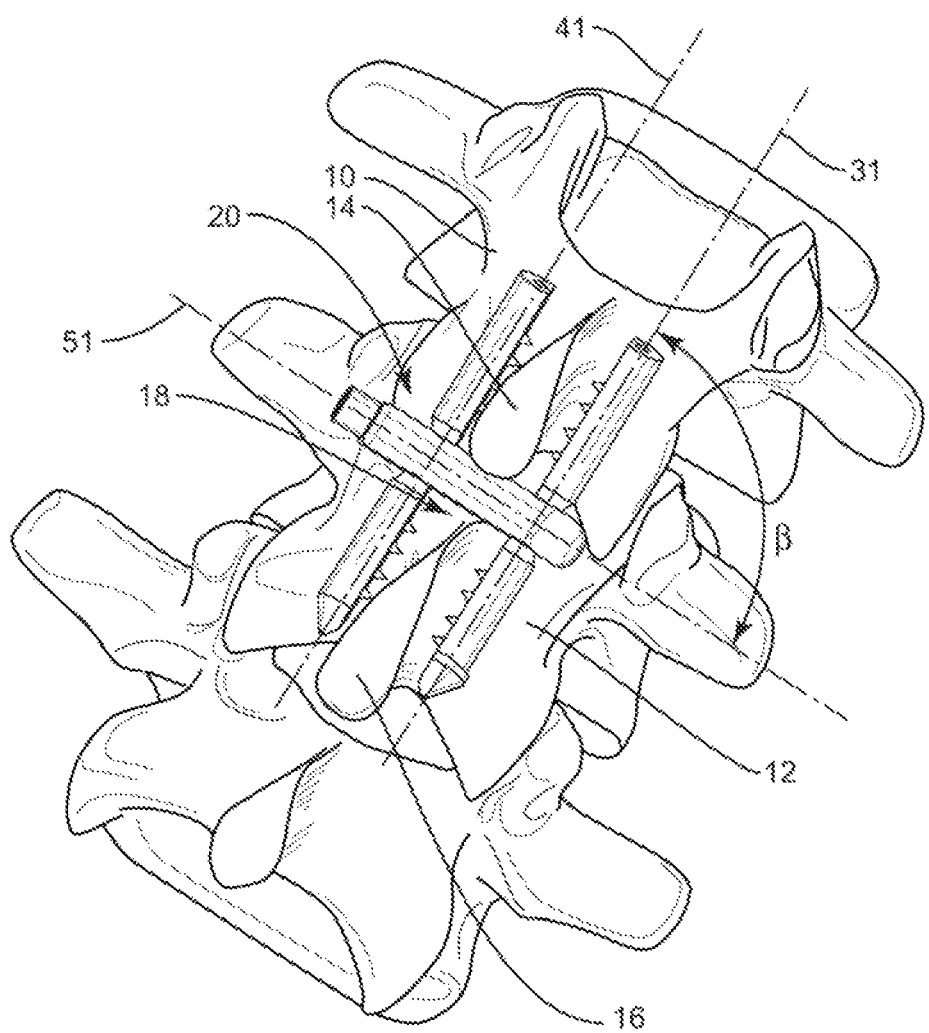
FIG. 1 shows a spinal motion segment with an implant according to one embodiment of the present invention prior to being clamped to the spinous processes.
Figure 2:
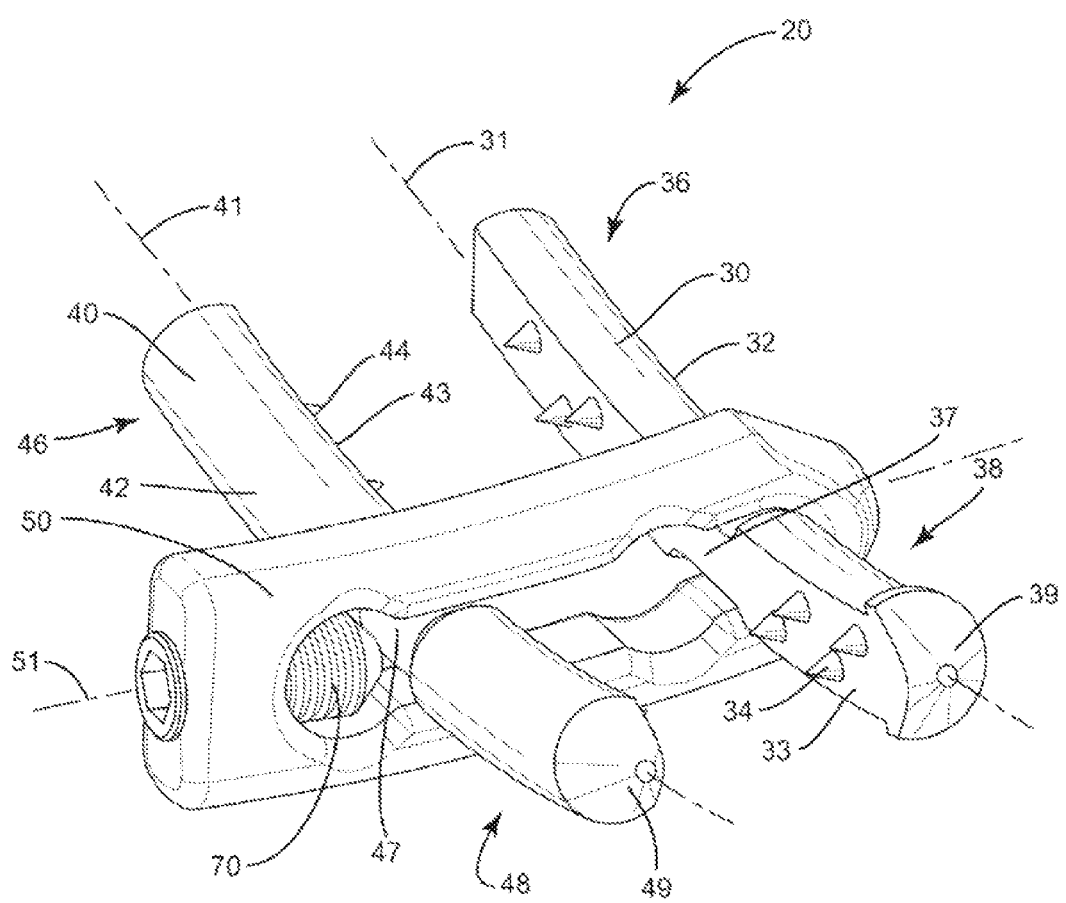
FIG. 2 shows the implant of FIG. 1 in a lateral perspective view.
Figure 3:
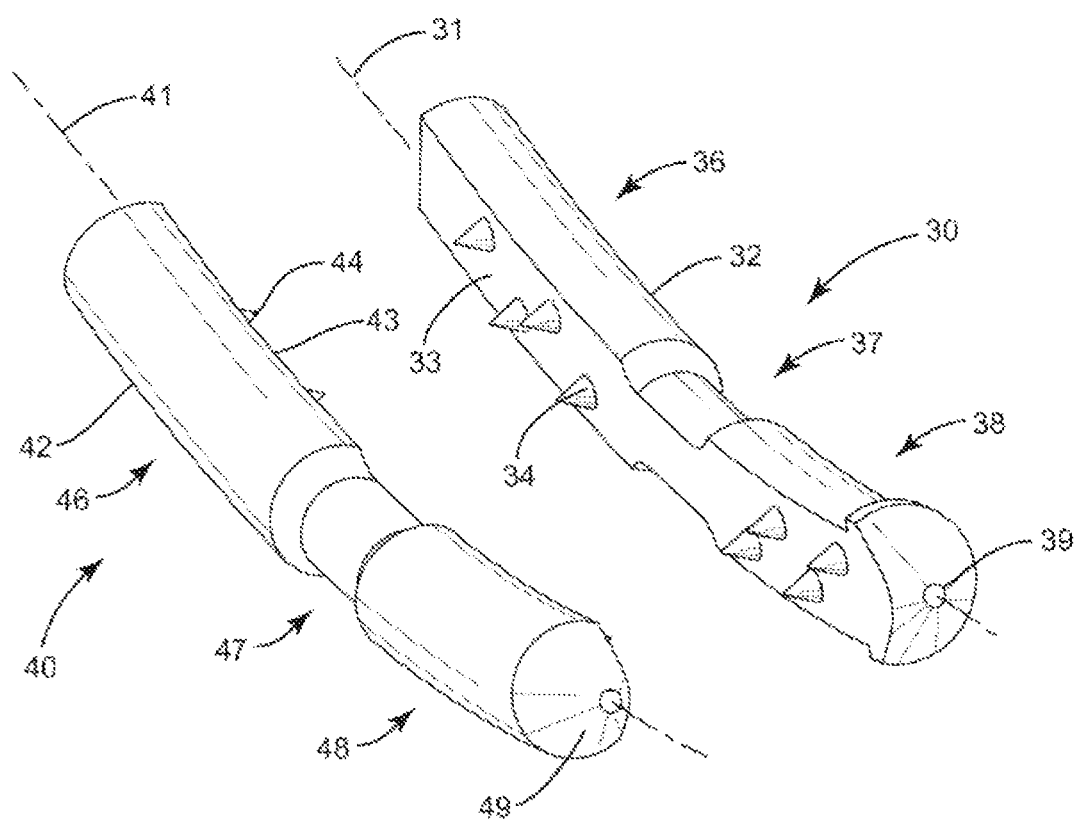
FIG. 3 shows the first and second plates of the implant of FIG. 1 in perspective view.

In one embodiment, the present invention is directed to an implant 20 for spinal fusion that attaches to adjacent spinous processes 14,16 to fixate the corresponding vertebrae 10,12 relative to the other. In at least one embodiment, the implant 20 includes two fixation plates 30,40 and an interconnecting frame 50. The fixation plates 30,40 are disposed on respective lateral sides of adjacent spinous processes 14,16, and the frame 50 extends laterally through the corresponding interspinous space 18. The fixation plates 30,40 and frame 50 are advantageously inserted, and locked together, using a percutaneous approach.

Figure 4:
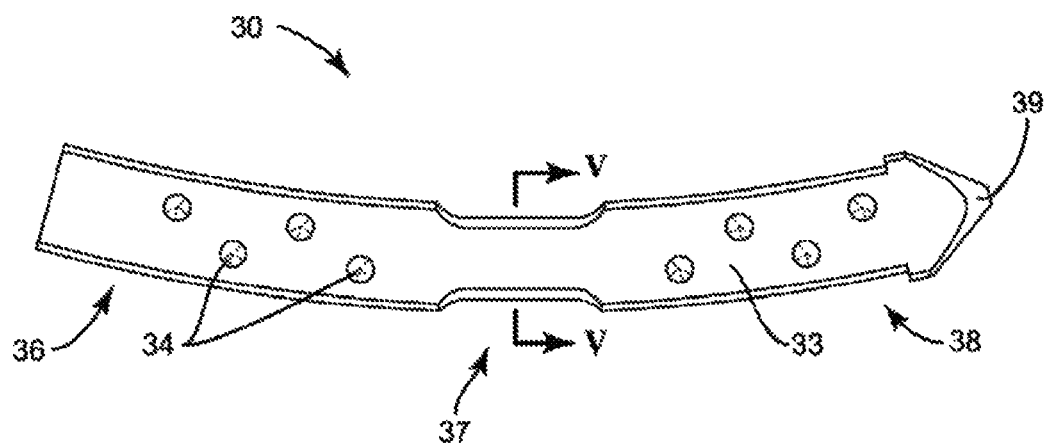
FIG. 4 shows the medial face of the first plate of the implant of FIG. 1.
Figure 5:
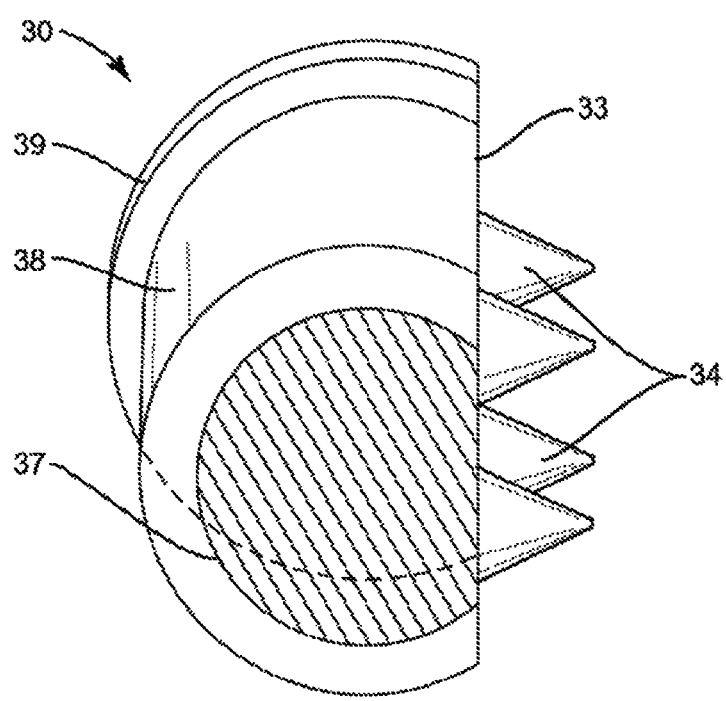
FIG. 5 shows a cross section of the first plate of the implant of FIG. 1 along line V-V of FIG. 4.

One embodiment of the implant 20 is shown in FIGS. 1-7. The implant 20 of FIG. 1 includes first and second plates 30,40, a frame 50, and a locking element 70. The first plate 30 is an elongate member that extends along a curving longitudinal axis 31. As such, the first plate 30 is longitudinally curving, as shown in FIG. 4. The first plate 30 may be divided into a superior section 36, an intervening intermediate section 37, and an inferior section 38, which are arranged sequentially in abutting relationship along the axis 31. As can be seen, the superior end may be relatively flat, while the inferior end advantageously is in the form of a tapering tip 39. The intermediate section 37 has a reduced cross section compared to the superior and inferior sections 36,38, advantageously with suitable smooth transitions therebetween. The main or base portion 32 of the first plate 30 has a generally flat medial face 33, and advantageously has a generally D-shaped cross section normal to the longitudinal axis 31. The medial face 33 has plurality projections or teeth thereon, which extend medially away from the longitudinal axis 31. These projections 34 are for biting into the spinous processes 14,16 when the implant 20 is clamped thereto, as discussed further below. The "diameter" of the base portion 32, excluding the tip 39 but including the teeth 34, is advantageously slightly smaller than the "diameter" of large part of tip 39, such that the base portion 32 fits within the profile of the tip 39 projected along the longitudinal axis 31. This arrangement allows the majority of the first plate 30 to be slid into a hollow delivery tube 142 (see further discussion below) leaving just the tip 39 exposed, with the tube 142 being not larger in diameter than the tip 39.

The second plate 40 is likewise an elongate member that extends along a curving longitudinal axis 41. As such, the second plate 40 is longitudinally curving. The second plate 40 may be divided into a superior section 46, an intervening intermediate section 47, and an inferior section 48, which are arranged sequentially in abutting relationship along the axis 41. As can be seen, the superior end may be relatively flat, while the inferior end advantageously is in the form of a tapering tip 49. The intermediate section 47 has a reduced cross section compared to the superior and inferior sections 46,48, advantageously with suitable smooth transitions therebetween. The main or base portion 42 of the second plate 40 has a generally flat medial face 43, and advantageously has a generally D-shaped cross section normal to the longitudinal axis 41. The medial face 43 has a plurality of projections or teeth 44 thereon, which extend medially away from the longitudinal axis 41. Like the teeth 34 of the first plate 30, the teeth 44 on the second plate 40 are for biting into the spinous processes 14,16 when the implant 20 is clamped thereto, as discussed further below. The "diameter" of the base portion 42, excluding the tip 49 but including the teeth 44, is advantageously slightly smaller than the "diameter" of large part of tip 49, such that the base portion fits within the profile of the tip 49 projected along the longitudinal axis 41. This arrangement allows the majority of the second plate 40 to be slid into a hollow delivery tube 142 leaving just the tip 49 exposed, with the tube 142 being not larger in diameter than the tip 49.

The first and second plates 30, 40 may be substantially mirror images of each other, although this is not required in all embodiments.

Figure 6:
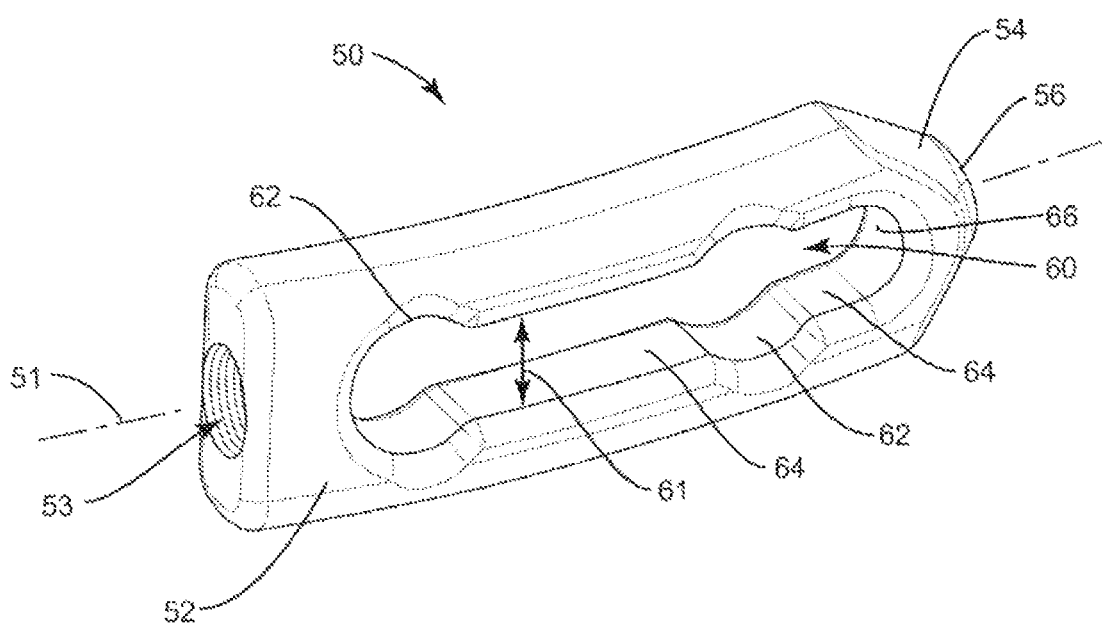
FIG. 6 shows the frame of the implant of FIG. 1
Figure 7:
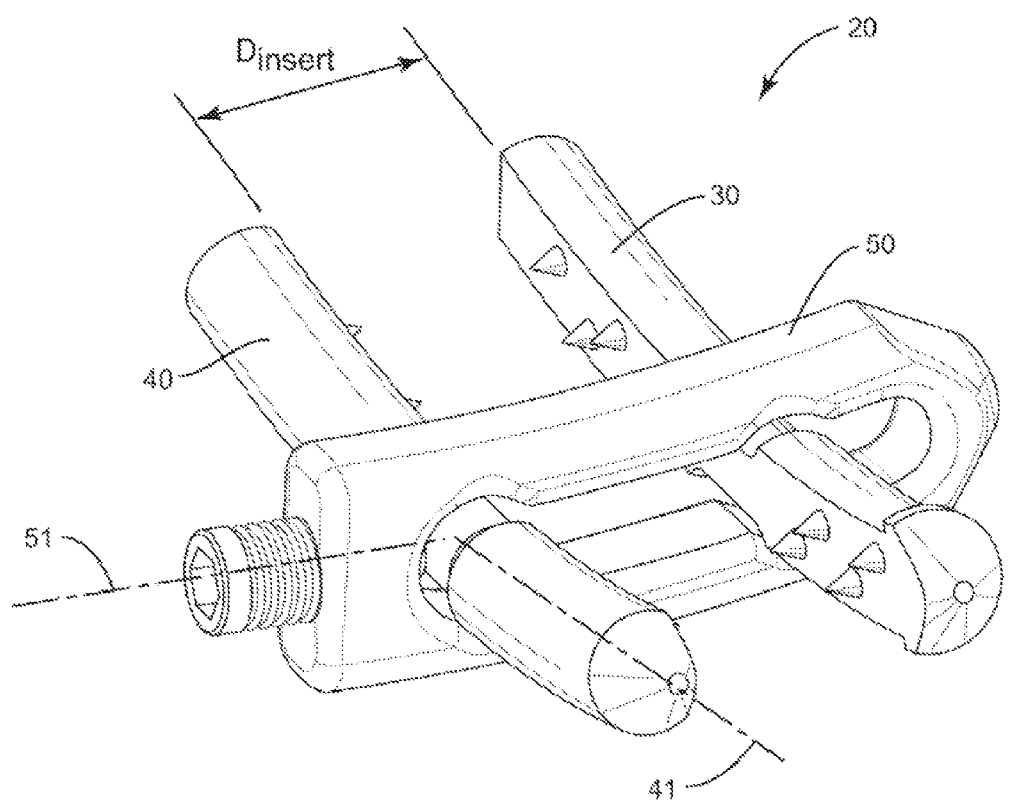
FIG. 7 shows the implant of FIG. 1 prior to clamping.
Figure 8:
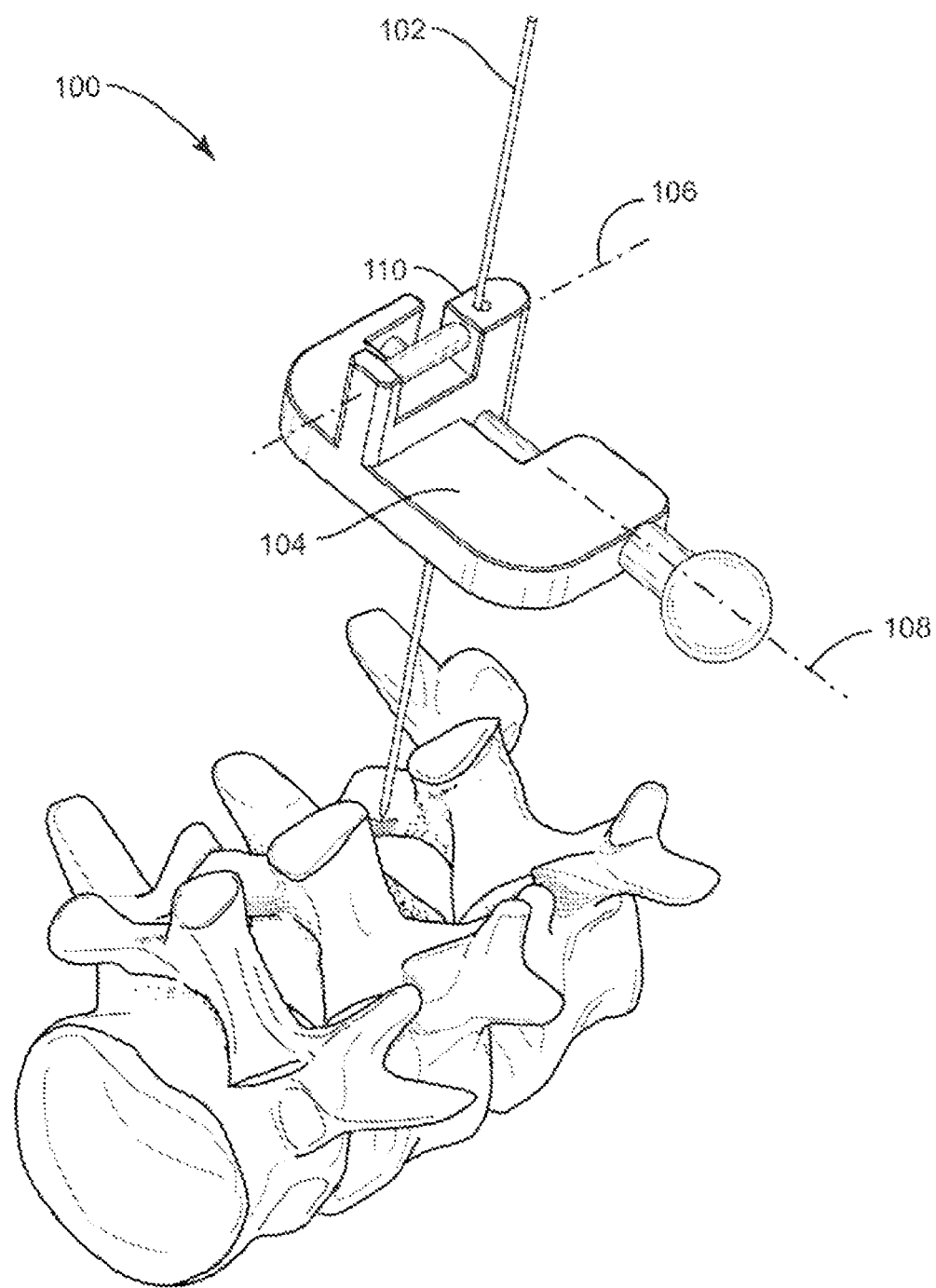
FIG. 8 shows a platform mounted to a guide pin.
Figure 9:
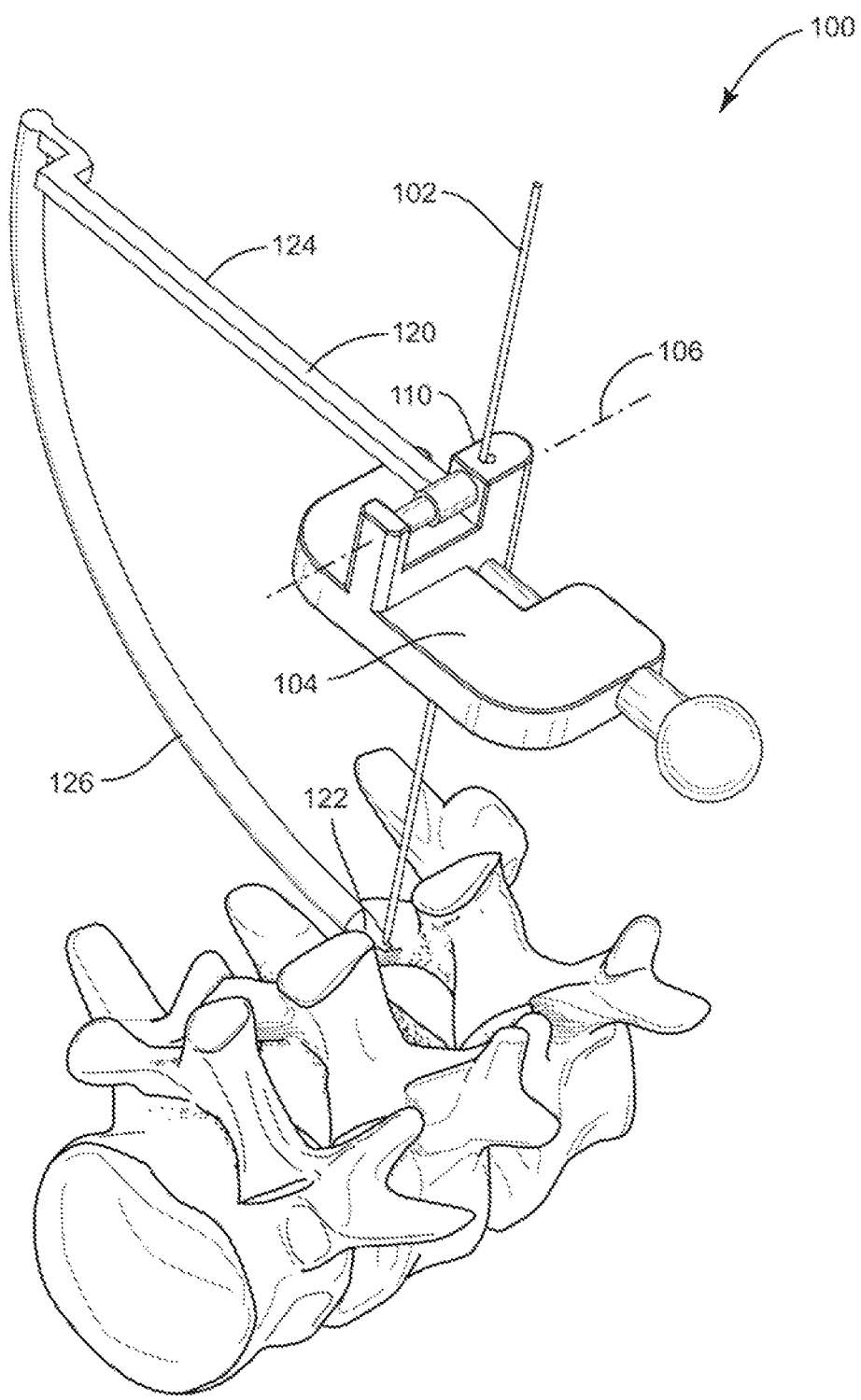
FIG. 9 shows a guide dilator positioned to the interspinous space.
Figure 10:
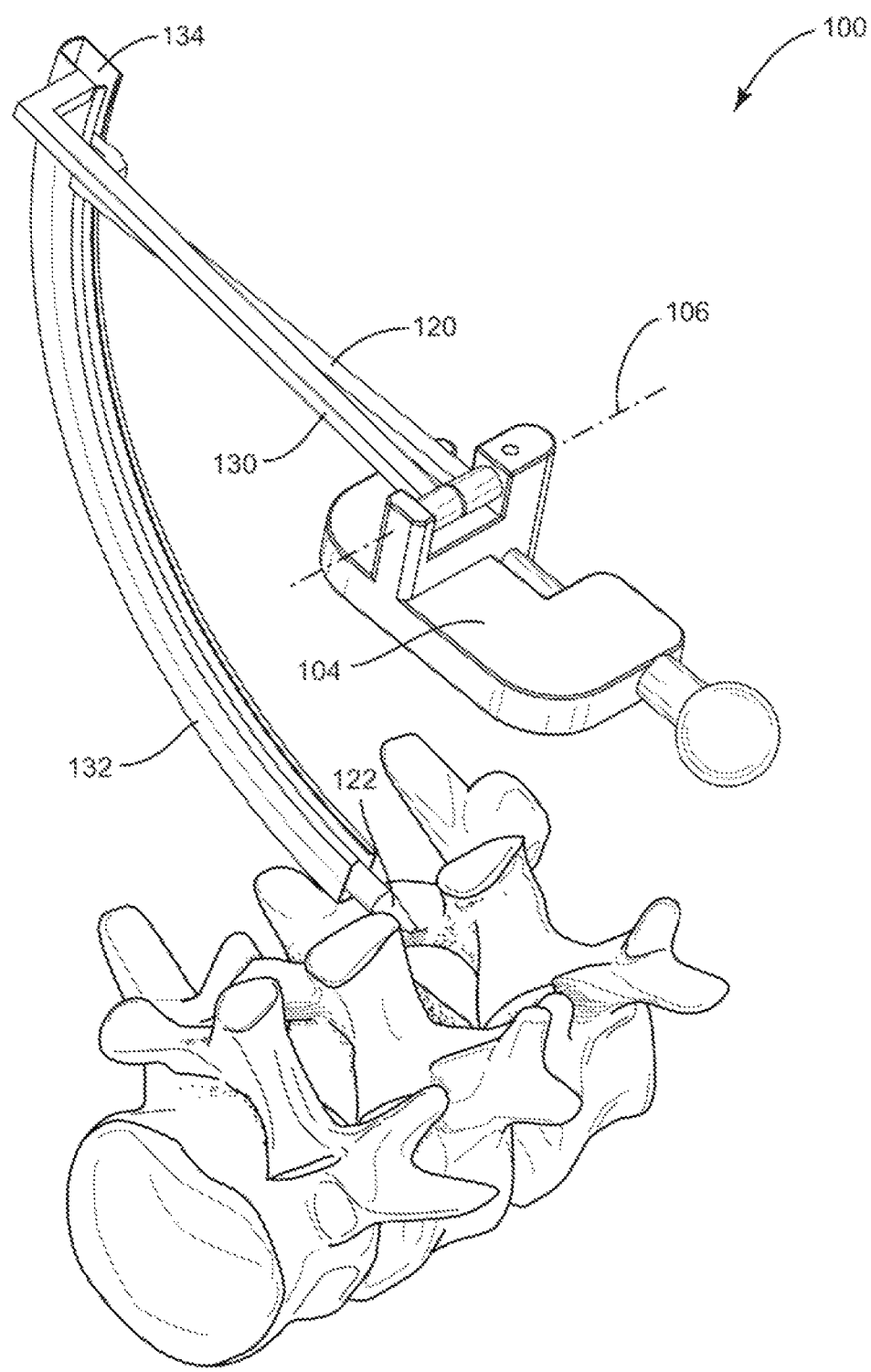
FIG. 10 shows the frame insertion swing arm disposed over the guide dilator.
Figure 11:
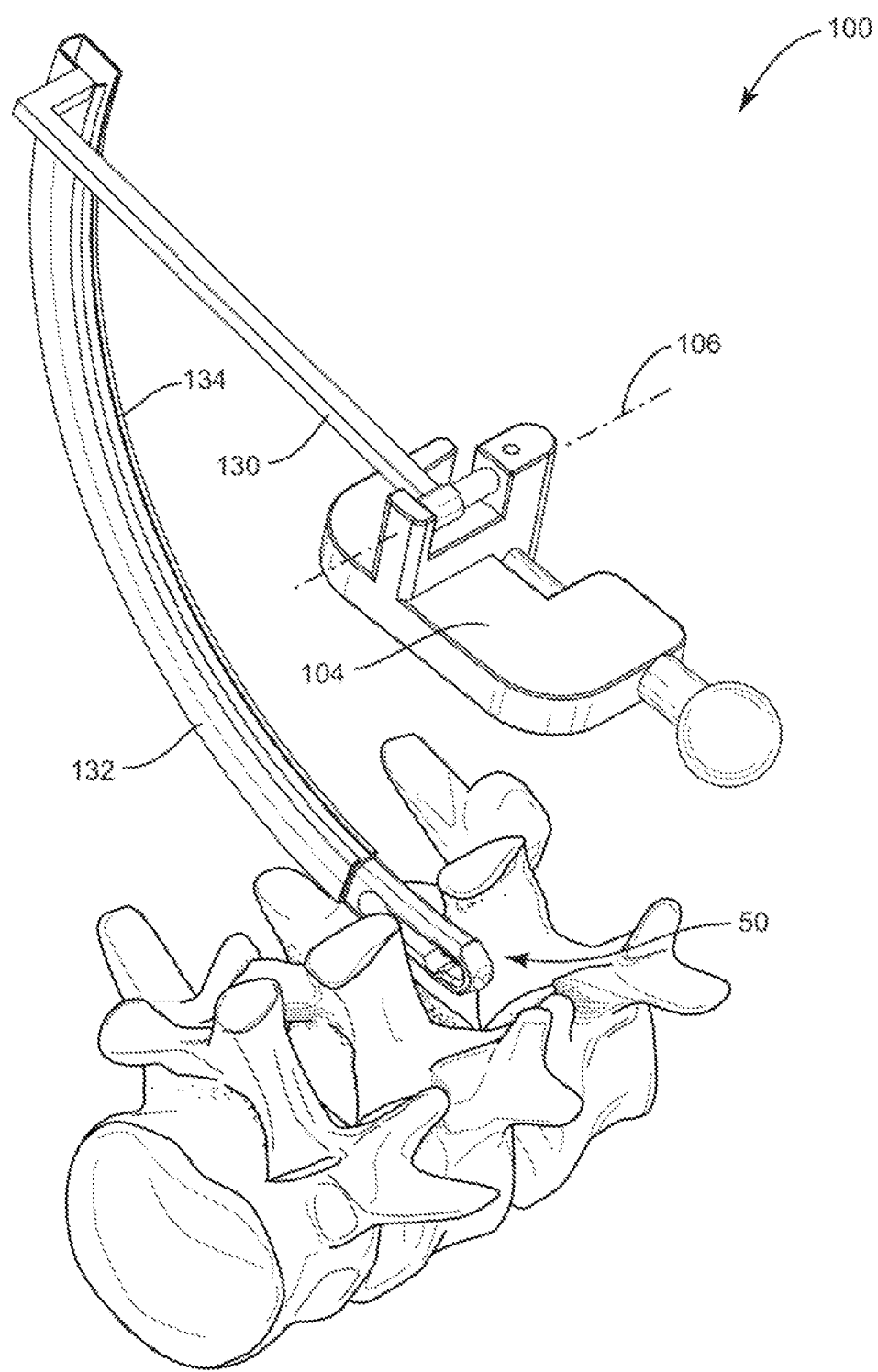
FIG. 11 shows the frame being positioned via the channel of the frame insertion swing arm.
Figure 12:
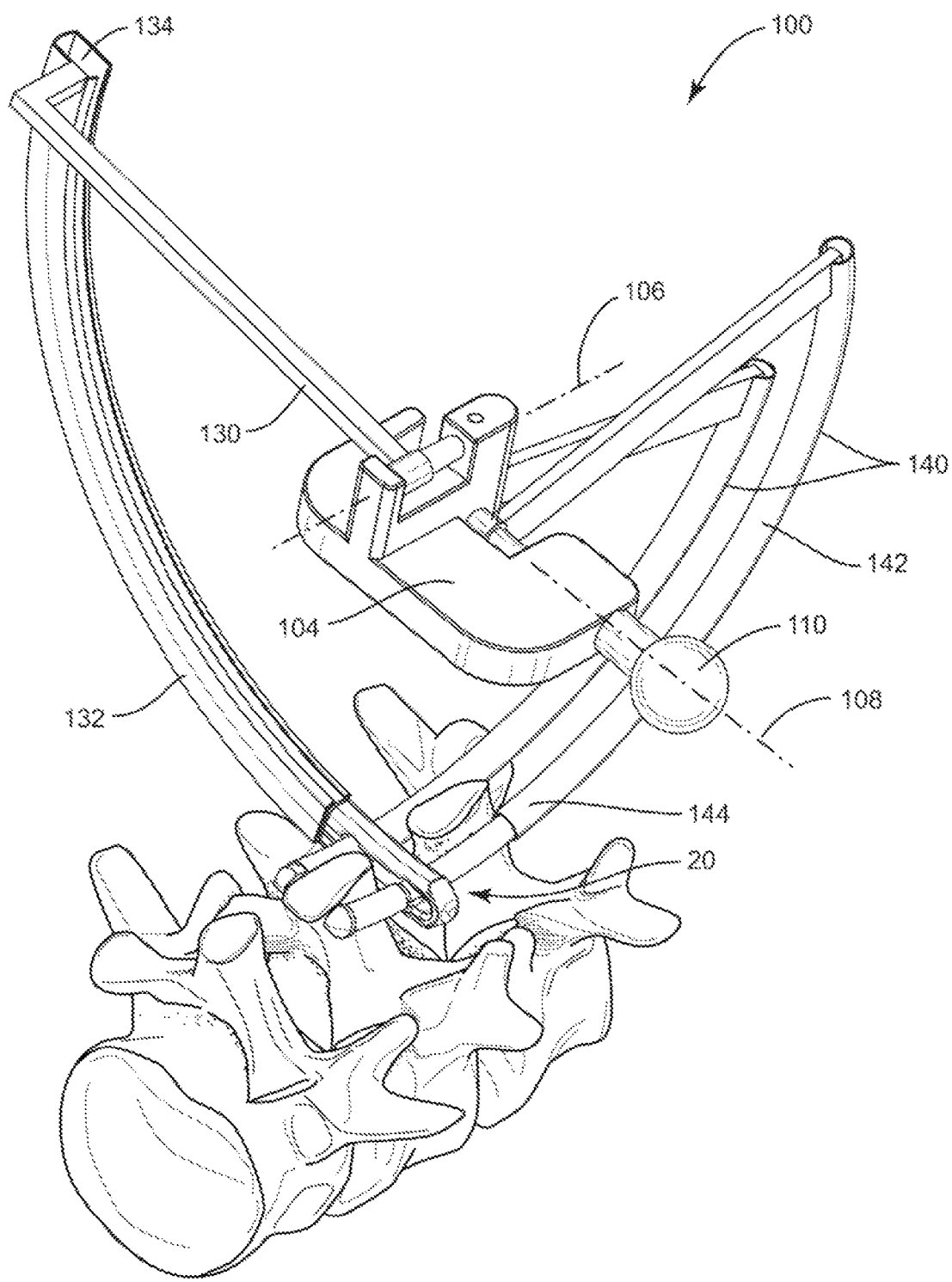
FIG. 12 shows insertion of the first and second plates disposed in the slot, with the plate insertion swing arm for the first plate partially removed to expose the first plate medial face.
Figure 13:
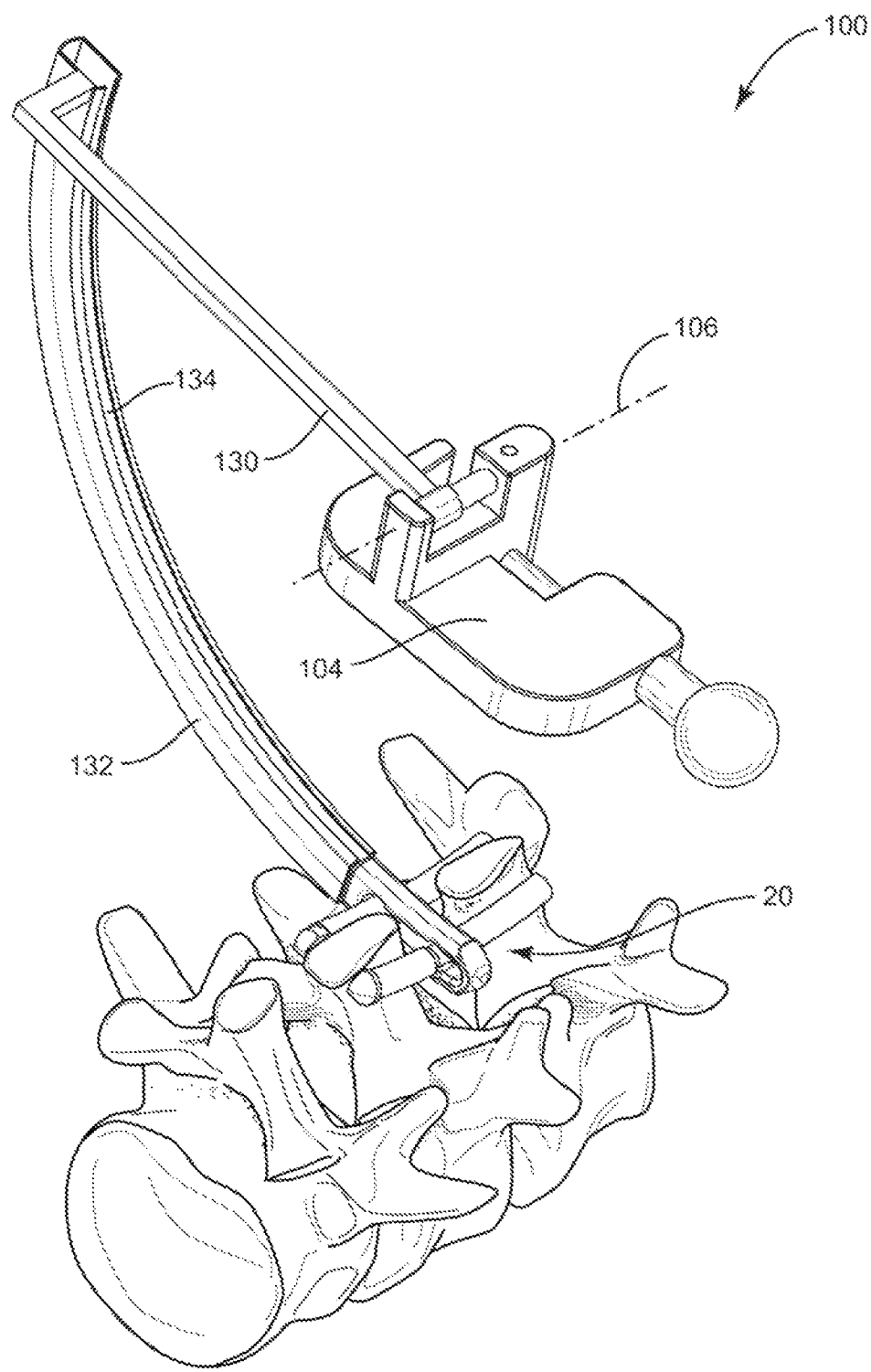
FIG. 13 shows insertion of the implant positioned after insertion of the first and second plates, prior to clamping.
Figure 14:
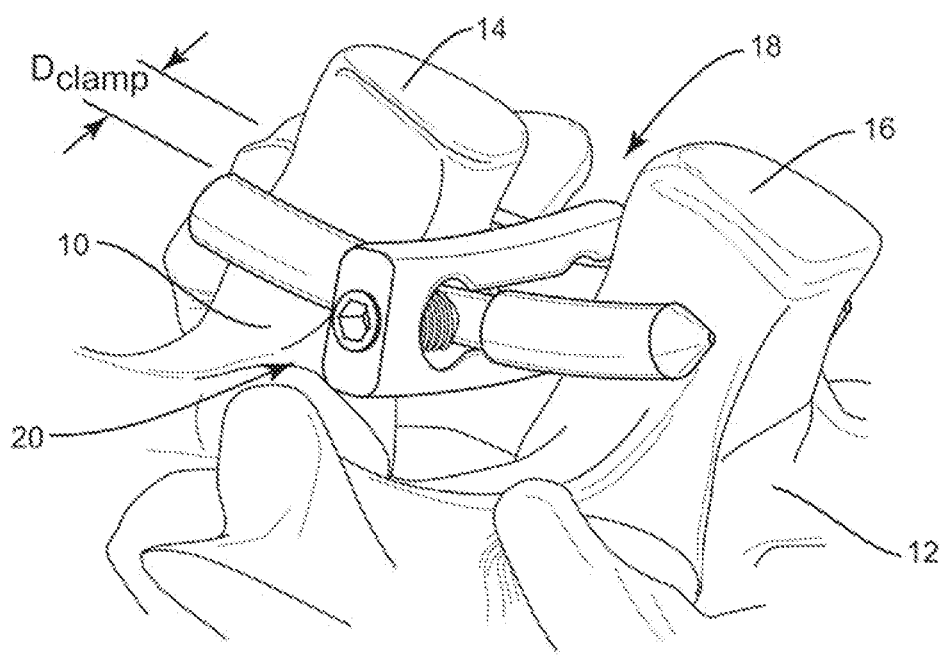
FIG. 14 shows the implant clamped to the spinous processes.

The frame 50 is an elongate member that advantageously extends along an associated longitudinal axis 51 from a proximal section 52 to a distal section 54, as shown in FIG. 6. The frame 50 includes a longitudinal slot 60 that is sized and configured to accept the first and second plates 30,40 therethrough, with the slot 60 being in both the proximal section 52 and the distal section 54. The slot 60 may be relatively uniform in height 61, but is advantageously variable in height. For example, FIG. 6 shows the slot 60 with two spaced apart enlarged height sections 62 interleaved with two spaced apart reduced height sections 64, with suitable smooth transitions therebetween. The proximal section 52 includes a longitudinal bore 52 extending into the slot 60. The bore 53 is sized and configured to engagingly receive the locking member 70, as described further below. Other than the bore 60, the distal and proximal ends of the slot 60 are advantageously fully enclosed. The distal section 54 advantageously tapers distally to form a tapered tip 56. The frame 50 is advantageously rigid, although flexible frames 50 may alternatively be used in some embodiments.

The locking element 70 helps clamp the first and second plates 30,40 to the spinous processes 14,16 by moving at least the second plate 40 longitudinally toward the first plate 30. The locking element 70 is illustrated as a setscrew, although other types of locking elements, such as barbed one-way pins, quarter-turn fasteners, and the like may alternatively be employed.

The implant 20 is formed of suitable biocompatible materials, such as stainless steel, titanium and its alloys, polymers such as PEEK, and the like.

The implant 20 may be implanted by positioning the frame 50 in the interspinous space 18 so that the longitudinal axis 51 passes through the sagittal plane defined by the adjacent spinous processes 14,16. The frame 50 should be oriented so that the slot height 61 is parallel to the anatomical axial plane. The locking element 70 is advantageously partially inserted into the bore 53 prior to the placement of the frame 50. The first and second plates 30,40 are then positioned transverse, e.g., perpendicular, to the frame 50, advantageously through the enlarged height sections 62 of the slot 60, so that each plate 30,40 extends proximate the superior and inferior spinous processes 14,16 on respective lateral sides thereof. Advantageously, the first and second plates 30,40 are disposed through the slot 60 so that the intermediate sections 38,48 rest in the corresponding enlarged height sections 62 of the slot 60. After insertion, prior to clamping, the first and second plates 30,40 are separated by a distance $D_{insert}$ (measured along axis 51). The locking element 70 is then advanced proximally relative to the frame 50 so as to apply a force to the second plate 40 along axis 51. This force is typically a result of the locking element 70 abutting the second plate 40 directly, but may be indirect, such as through an intervening shim, if desired. This force causes second plate 40 to displace distally out of enlarged section 62 and into the distally adjoining reduced section 64. As the second plate 40 presses against the spinous processes 14,16, the displacement force of the locking element 70 causes the frame 50 to in effect "pull back" so that the distal tip 56 of the frame 50 is moved closer to the sagittal plane through the interspinous space 18. This causes the first plate 30 to move out of its corresponding enlarged section 62 of the slot 60 and into the distally adjoining reduced section 64. Further displacement of the frame 50 causes the plates 30,40 to be clamped to the spinous processes 14,16, with the teeth 34,44 of the plates 30,40 biting into the spinous processes 14,16. When clamped, the first and second plates 30,40 are separated by a distance $D_{clamp}$, which is smaller than distance $D_{insert}$. This clamping of the implant 20 to the spinous processes 14,16 immobilizes the spinous processes 14,16 relative to each other, thereby stabilizing the vertebrae 10,12 and the corresponding disc space suitably for fusion to occur.

The above process may be carried out using a relatively large access with a posterior approach, similar to that described in U.S. Pat. Nos. 7,048,736 and 7,727,233. However, the implantation process is advantageously carried out percutaneously, as described further below.

The implant 20 may be percutaneously implanted using an installation assembly 100 as shown in FIGS. 8-14. A reference guide, such as a Steinman pin 102, is directed to the desired interspinous space 18. A platform 104 is then secured to the pin 102, such as by routing the pin 102 trough a pin boss 110 on the platform 104 and securing the platform 104 thereto. The platform 104 is advantageously mounted to the pin 102 at a predetermined height along the pin 102 that allows the swing arm installation described below to position the components of the implant 20 as desired. It should be understood that the platform 104 is also supported by ways not shown, such as legs and the like, to the surgical table. The position of the platform 104 is locked relative to the patient and the surgical table once positioned properly on the pin 102. As such, the pin 102 may be removed at this point of the surgical procedure if desired. A guide dilator 120 is then attached to the platform 104 so that it rotates about an axis 106 parallel to the spinal column. The guide dilator 120 has a tapered tip 122, and includes a pivot arm section 124 and a curvate section 126. The pivot arm section 124 extends outward from the platform 104, and advantageously includes a short jog section as illustrated. The curvate section 126 is curved at a uniform radius of curvature that enables the tip 122 to stop in the desired interspinous space 18 when the platform 104 is positioned correctly. If not previously removed, the pin 102 should be removed at this point in the procedure. A frame insertion swing arm 130 is then attached to the platform 104. The frame insertion swing arm 130 includes a curvate guide tube 132 with a channel 134. The guide dilator 120 slides within the channel 134 to guide the distal end of the frame insertion swing arm 130 to the desired location. The guide dilator 120 is then removed and the frame 50 inserted into the channel 134. The frame 50 is then advanced down the channel 134 using any suitable means until the frame 50 is properly disposed through the interspinous space 18. A plate insertion swing arm 140 is then attached to the platform 104 for rotation about a laterally running axis. The plate insertion swing arm 140 includes a curved hollow tube 142 that curves at a suitable rate to extend through the frame slot 60 when swung into position. The first plate 30 is advantageously preloaded into the distal portion of the hollow tube 142 before rotating the plate insertion swing arm 130 down into position. The tip 39 of the first plate 30 is tapered, as discussed above, in order to dilate the affected tissue during this swinging action. The tissue is protected from the teeth 34 of the first plate 30 because the teeth 34 are disposed inside the hollow tube 142. Similarly, another plate insertion swing arm 140 is used to insert the second plate 40 through the slot 60 of the frame 50. Once the plates 34,40 are positioned properly through the slot 60, the plate insertion swing arms 140 are rotated back out of position while using a suitable push rod or the like to expel the plates 30,40 from the corresponding hollow tubes 142. The plate insertion swing arms 140 are then removed from the platform 104. A suitable tool (not shown) is then advanced through the channel 134 to actuate the locking mechanism 70 to clamp the implant 20 to the spinous processes 14,16. The frame insertion swing arm 130 is then removed, followed by the pin 102. Such a procedure may be accomplished with three small incisions, one each for the frame 50 and the two plates 30,40. Each of the components of the implant 20 is implanted using a percutaneous, swing arm-based approach to properly position the components, and subsequently clamp the implant 20 in position. The use of such a percutaneous method allows for less surgical damage and quicker recovery.

The swing arms 130,140 and guide dilator 120 discussed above may be pivotally mounted to the platform 104 in any suitable fashion, such as via C-shaped snap on sections, clamshell connectors, or the like. The swing arms 130,140 and guide dilator 120 discussed above may also have corresponding positive stops (not shown) on the platform 104 to prevent over-rotating them beyond their respective desired positions.

The angle β between the frame axis 51 and the axis 31 of first plate 30 (or axis 41 of second plate 40) may be 90°, i.e. perpendicular. However, the reduced cross sectional shape of the intermediate sections 37,47 not only allows the plates 30,40 to be moved into the reduced height sections 64 of slot 60, but also allows for small angular variations, such as ±15° or less from perpendicular, for angle β so as to accommodate spinal morphological variations between the vertebrae 10,12.

The discussions above have been in the context of the plates 30,40 having teeth 34,44 generally arranged in an array on their medial faces 33,43. However, other arrangements may be used, and any suitable form of biting projections may alternatively be employed.

All U.S. patents and patent application publications mentioned above are hereby incorporated herein by reference in their entirety.

The present invention may, of course, be carried out in other specific ways than those herein set forth without departing from the scope of the invention. The present embodiments are, therefore, to be considered in all respects as illustrative and not restrictive, and all changes coming within the meaning and equivalency range of the appended claims are intended to be embraced therein.

What is claimed is:
1. A spinal implant device comprising:
a first plate includes first and second end sections, with an intermediate portion disposed therebetween and the first plate curvingly extending along a first curved longitudinal axis such that the first end, the second end and the intermediate portion of the first plate form an arcuate shape along a length of the first plate and having a first medial face configured to abut adjacent spinous processes and having biting projections thereon;

a second plate includes first and second end sections, with an intermediate portion disposed therebetween and the second plate curvingly extending along a second curved longitudinal axis such that the first end, the second end and the intermediate portion of the second plate form an arcuate shape along a length of the second plate and having a second medial face configured to abut the adjacent spinous processes and having biting projections thereon;

a frame extending along a third curved longitudinal axis and having a longitudinal slot therethrough;

the first and second plates disposed through the slot such that the first and second axes are transverse to the third axis and the first and second medial faces face toward each other in spaced relation;

a locking element engaging a proximal end of the frame and longitudinally moveable relative to the frame such that longitudinal displacement of the locking element toward a distal end of the frame narrows a distance between the first plate and the second plate.

2. The spinal implant of claim 1 wherein longitudinal displacement of the locking element toward a distal end of the frame causes the first and second plates to enter relatively narrower sections of the slot.

3. The spinal implant of claim 1: wherein the intermediate portion has a reduced cross section relative to the first and second end sections; wherein the intermediate section is disposed in the slot.

4. The spinal implant of claim 3 wherein the first end section of the first plate has a tapered tip portion disposed opposite the intermediate section.

5. The spinal implant of claim 4 wherein the tapered tip portion has the largest cross section of the first plate.

6. The spinal implant of claim 1 wherein the first plate comprises an elongate base and the associated biting projections; wherein the base has a substantially D-shaped cross-section normal to the first axis, with the medial face being substantially flat.

7. The spinal implant of claim 1 wherein the slot has a variable height.

8. The spinal implant of claim 7 wherein the slot comprises two portions of enlarged height, disposed in longitudinally spaced relation.

9. The spinal implant of claim 1 wherein the first and second plates are substantially mirror images of each other.

10. The spinal implant of claim 1 wherein the locking element is a screw.

11. The spinal implant of claim 1 wherein the frame further comprises proximal and distal longitudinal sections; wherein the distal section comprises a tip that tapers away from the proximal section; wherein the slot extends in both the proximal and distal sections.

12. The spinal implant of claim 11 wherein the proximal section comprises a longitudinally extending bore sized and configured to engagingly receive the locking element.

13. The spinal implant of claim 1 wherein the locking element abuts the second plate.

14. The spinal implant of claim 1 wherein the first and second axes are substantially perpendicular to the third axis.

15. A spinal implant, comprising:
a first plate includes first and second end sections, with an intermediate portion disposed therebetween and the first plate curvingly extending along a first curved longitudinal axis such that the first end, the second end and the intermediate portion of the first plate form an arcuate shape along a length of the first plate; the first plate having a first medial face configured to abut adjacent spinous processes with biting projections thereon;

a second plate includes first and second end sections, with an intermediate portion disposed therebetween and the second plate curvingly extending along a second curved longitudinal axis such that the first end, the second end and the intermediate portion of the second plate form an arcuate shape along a length of the second plate; the second plate having a second medial face configured to abut the adjacent spinous processes with biting projections thereon;

a curvilinear frame extending along a third curved longitudinal axis and having a longitudinal slot therethrough;

the first and second plates disposed through the slot such that the first and second axes are transverse to the third axis and the first and second medial faces face toward each other in spaced relation;

a locking element engaging a proximal end of the frame and longitudinally moveable relative to the frame;

the implant changeable from a first configuration to a second configuration;

wherein, in the first configuration, the first and second plates are disposed a first distance apart;

wherein, in the second configuration:
the first and second plates are disposed a second distance apart, the second distance less than the first distance;
the first and second plates are disposed more distally relative to frame than in the first configuration;
the locking element is disposed more distally relative to the frame than in the first configuration.

16. The spinal implant of claim 15 wherein the slot comprises a distal end; wherein the first plate abuts the distal end of the slot in the second configuration; wherein the locking element abuts the second plate in the second configuration.

17. The spinal implant of claim 15: wherein the intermediate portion has a reduced cross section relative to the first and second end sections; wherein the intermediate section is disposed in the slot.

18. The spinal implant of claim 15 wherein the first and second plates are disposed substantially perpendicular to the third axis.

19. The spinal implant of claim 15 wherein the slot has variable height, with two spaced apart first sections of enlarged height and two spaced apart second sections of reduced height; wherein one of the second sections of reduced height is disposed between the first sections of enlarged height; wherein one of the first sections is disposed between the second sections.

20. The spinal implant of claim 19 wherein the first and second plates are disposed in the first sections of the slot in the first configuration; wherein the first and second plates are disposed in the second sections of the slot in the second configuration.

* * * * *